United States Patent
Nickey et al.

(10) Patent No.: US 6,848,564 B2
(45) Date of Patent: *Feb. 1, 2005

(54) METHOD AND APPARATUS FOR INSPECTING ARTICLES OF GLASSWARE

(75) Inventors: George A. Nickey, Maumee, OH (US); Stephen M. Gerber, Petersburg, MI (US); Noel D. Wendt, Toled, OH (US); Ronald E. Gast, Genoa, OH (US); Gregory A. Ritz, Berkey, OH (US); James Scott Barnes, Maumee, OH (US); William R. Martin, Slippery Rock, PA (US)

(73) Assignee: Owens-Brockway Glass Container Inc., Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/733,006

(22) Filed: Dec. 11, 2003

(65) Prior Publication Data

US 2004/0118162 A1 Jun. 24, 2004

Related U.S. Application Data

(62) Division of application No. 10/395,907, filed on Mar. 24, 2003, now Pat. No. 6,745,890, which is a division of application No. 09/679,584, filed on Oct. 4, 2000, now Pat. No. 6,581,751.

(51) Int. Cl.[7] ............................................. B65G 47/24
(52) U.S. Cl. .................................. 198/379; 198/803.11
(58) Field of Search ........................... 198/379, 803.11, 198/473.1

(56) References Cited

U.S. PATENT DOCUMENTS

| | | |
|---|---|---|
| 1,309,935 A | 7/1919 | Culleson |
| 2,349,638 A | 5/1944 | Schreiber |
| 2,393,188 A | 1/1946 | Reynolds |
| 2,682,802 A | 7/1954 | Fedorchak et al. |
| 3,074,531 A | 1/1963 | Pechy |
| 3,133,638 A | 5/1964 | Calhoun |
| 3,279,599 A | 10/1966 | Drennan |
| 3,313,409 A | 4/1967 | Johnson |
| 3,351,198 A | 11/1967 | Wyman |
| 3,382,974 A | 5/1968 | Mayeux |
| 3,599,780 A | 8/1971 | Sorbie |
| 3,601,616 A | 8/1971 | Katsumata |
| 3,651,937 A | 3/1972 | Kronseder |
| 3,655,064 A | 4/1972 | Mayer |
| 3,782,542 A | 1/1974 | Scribner |
| 3,811,567 A | 5/1974 | Tomita et al. |
| 3,827,812 A | 8/1974 | Heimann |
| 3,879,993 A | 4/1975 | Sorbie |
| 3,886,356 A | 5/1975 | Gomm |
| 3,923,158 A | 12/1975 | Fornaa |
| 3,941,686 A | 3/1976 | Juvinal |
| 3,963,348 A | 6/1976 | Nakatani et al. |
| 3,975,260 A | 8/1976 | Peyton et al. |
| 4,029,958 A | 6/1977 | Wright |

(List continued on next page.)

Primary Examiner—Joe Dillon, Jr.

(57) ABSTRACT

Apparatus for indexing glassware through a series of angularly spaced stations includes first and second arrays of glassware gripping fingers mounted on associated carriers that are rotatable about a common axis, both conjointly and with respect to each other. Each carrier is connected to as associated servo motor, which in turn are connected to a controller for rotating the carriers with respect to each other to grip and release glassware between the fingers, and to rotate the carriers conjointly to index the glassware between apparatus stations. One array of glassware gripping fingers includes coil springs for biasing the fingers toward the fingers of the opposing array for accommodating tolerance variations in the glassware. Drive rollers are located at at least some of the stations, and are pivotal into and out of positions for rotating the containers about their axes for inspection or other purposes.

21 Claims, 18 Drawing Sheets

U.S. PATENT DOCUMENTS

| | | |
|---|---|---|
| 4,055,252 A | 10/1977 | Klamm et al. |
| 4,075,086 A | 2/1978 | Marsh, III et al. |
| 4,124,112 A | 11/1978 | Mohney et al. |
| 4,172,524 A | 10/1979 | Holm et al. |
| 4,200,183 A | 4/1980 | Riggs |
| 4,230,219 A | 10/1980 | Pezzin et al. |
| 4,241,256 A | 12/1980 | Tagaya et al. |
| 4,249,075 A | 2/1981 | Lovalenti |
| 4,368,641 A | 1/1983 | McLeod |
| 4,378,493 A | 3/1983 | Dorf et al. |
| 4,391,372 A | 7/1983 | Calhoun |
| 4,433,785 A | 2/1984 | Riggs |
| 4,442,934 A | 4/1984 | Dorf |
| 4,579,227 A | 4/1986 | Miller |
| 4,596,107 A | 6/1986 | Pfleger, Sr. |
| 4,601,395 A | 7/1986 | Juvinall et al. |
| 4,636,635 A | 1/1987 | Krönseder |
| 4,731,649 A | 3/1988 | Chang et al. |
| 4,852,415 A | 8/1989 | Bogatzki et al. |
| 4,912,318 A | 3/1990 | Kajiura et al. |
| 4,915,237 A | 4/1990 | Chang et al. |
| 5,392,928 A | 2/1995 | Nickey et al. |
| 5,404,227 A | 4/1995 | Sumita et al. |
| 5,459,313 A | 10/1995 | Schrader et al. |
| 5,560,473 A | 10/1996 | Ivancso |
| 5,719,679 A | 2/1998 | Shimizu et al. |
| 5,772,001 A | 6/1998 | Otruba et al. |
| 6,557,665 B2 | 5/2003 | Gerber |

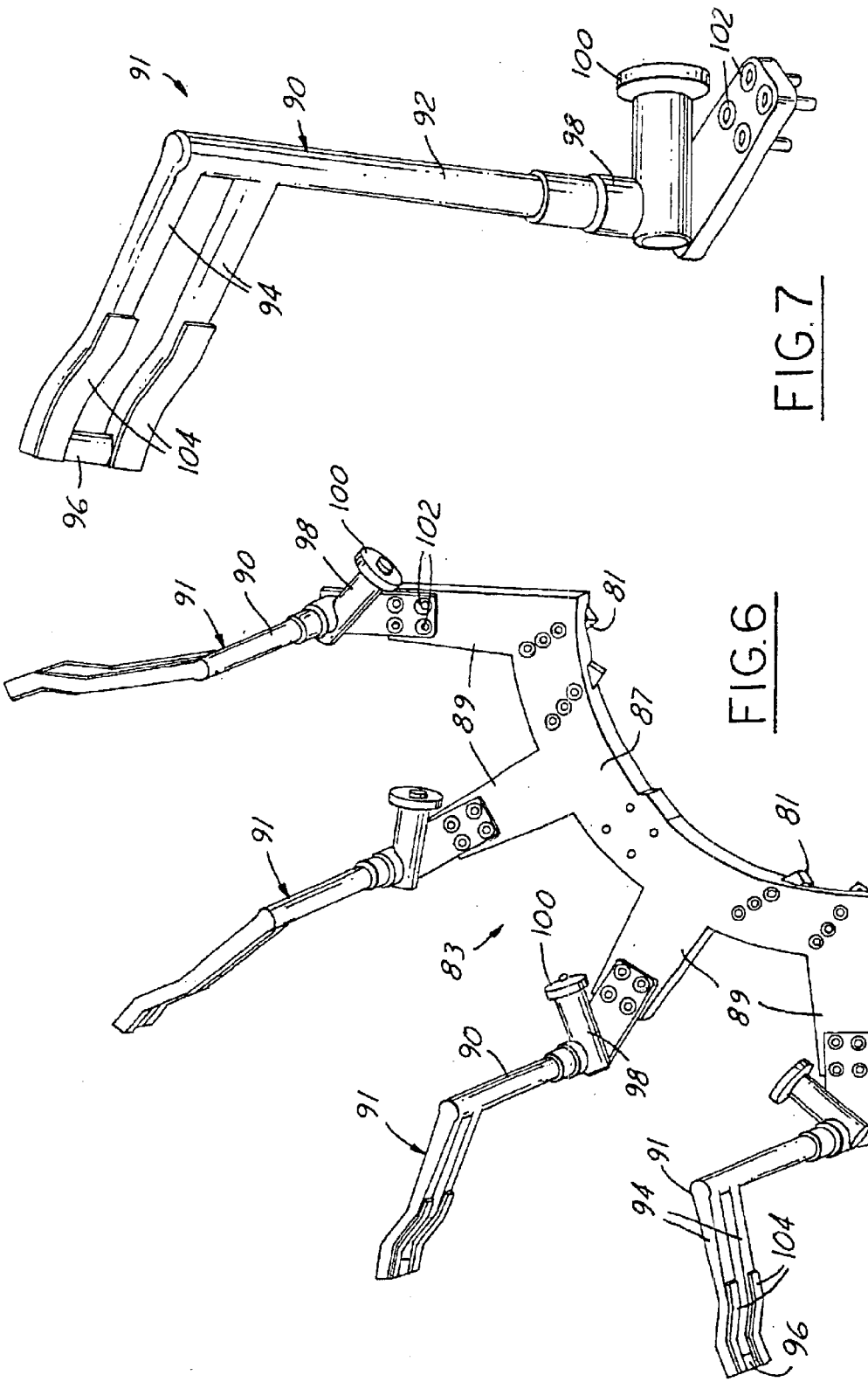

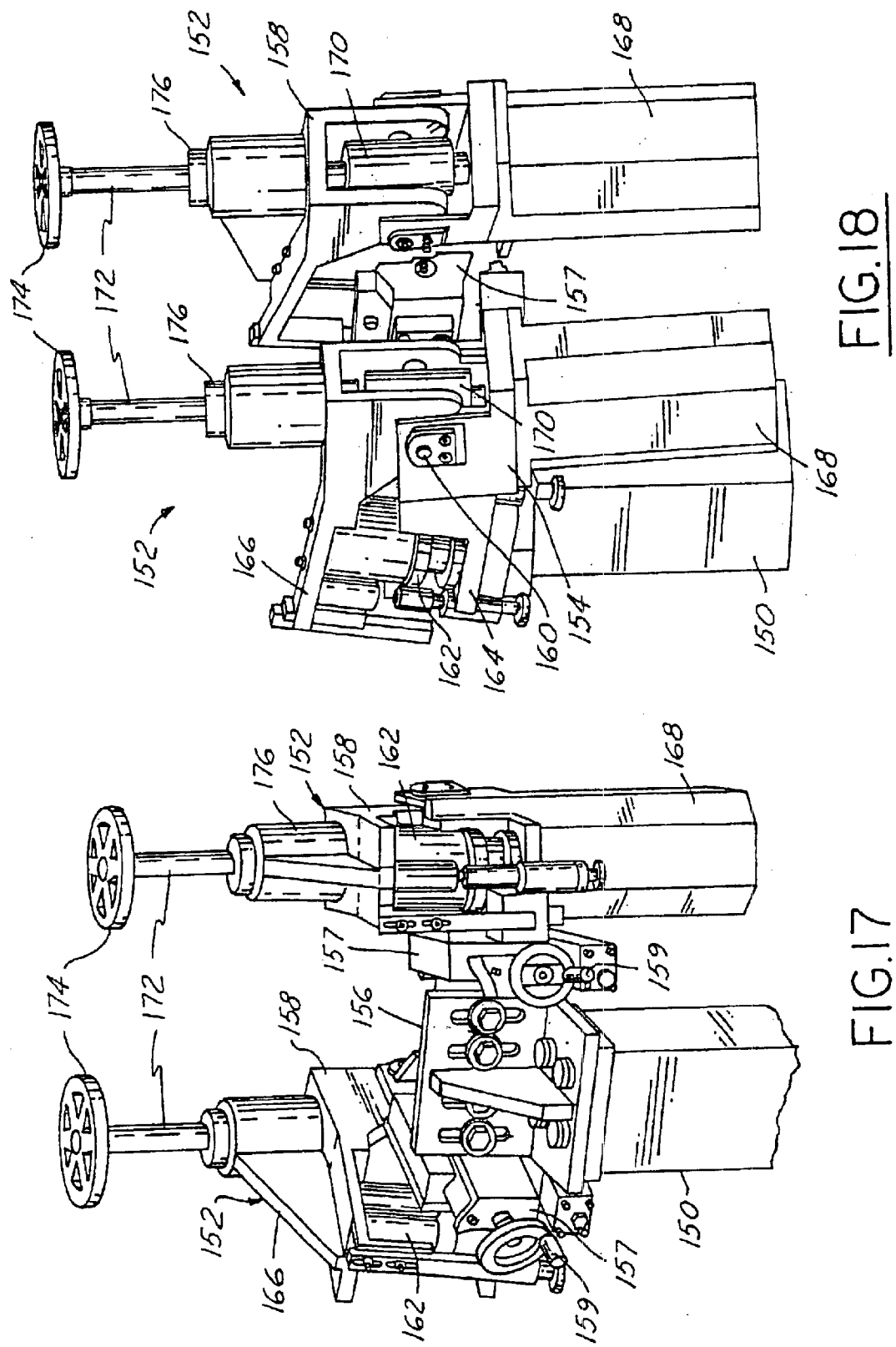

METHOD AND APPARATUS FOR INSPECTING ARTICLES OF GLASSWARE

This application is a division of application Ser. No. 10/395,907 filed Mar. 24, 2003, now U.S. Pat. No. 6,745,890, which is a division of application Ser. No. 09/679,584 filed Oct. 4, 2000, now U.S. Pat. No. 6,581,751.

The present invention is directed to inspection of glassware articles such as glass containers, and more particularly to a method and apparatus for conveying articles of glassware through a series of inspection stations.

BACKGROUND AND SUMMARY OF THE INVENTION

In the manufacture of glassware, such as glass containers, various anomalies or variations can occur that affect commercial accept ability of the containers. These anomalies, termed "commercial variations," can involve dimensional characteristics of the container such as at the container finish, surface characteristics that can affect acceptable operation of the container such as surface variations at the container sealing surface, or variations such as stones or checks within the container finish, sidewall or bottom. It is also conventional practice to mold indicia on each container indicative of the mold of origin of the container for inspection and quality control purposes. U.S. Pat. No. 4,378,493 illustrates a starwheel-type conveyor for accepting containers in sequence from an infeed conveyor and transporting the containers through a series of inspection stations. At at least some of the inspection stations, the container is held in position and rotated about its central axis while being electro-optically inspected for commercial variations and/or mold code. The term "inspection" is used in its broadest sense to encompass any optical, electro-optical, mechanical or electrical observation or engagement with the container to measure or determine a potentially variable characteristic, including but not necessarily limited to mold codes and commercial variations.

It is a general object of the present invention to provide an apparatus and method for indexing articles of glassware such as glass containers through a series of stations, such as stations at which the containers are to be inspected for commercial variations and/or reading the mold of origin of the containers. Among more specific objects of the invention are to provide such a method and apparatus that are characterized by increased speed of conveyance and therefore increased throughput through the inspection stations, that are versatile and accommodate a wide variety of optical, electro-optical, electrical or mechanical inspection techniques at the individual stations, that accommodate an increased number of inspection stations, preferably including all necessary inspections in a single machine, that provide unobstructed view of the container for increased versatility of electro-optical inspection, and/or that accommodate containers of differing diameter and height.

Apparatus for indexing glassware such as containers through a series of stations, such as electro-optical or mechanical inspection stations, in accordance with a presently preferred embodiment of the invention includes first and second circumferential arrays of alternately opposed glassware gripping fingers mounted on associated first and second carriers. The carriers are rotatable on a common axis, with at least one of the carriers being rotatable with respect to the other for moving the fingers of the associated arrays toward and away from each other to grip and release glassware. The carriers are also rotatable conjointly about the common axis to transport each glassware article through the series of stations. In the preferred embodiment of the invention, each carrier is coupled to an associated motor for rotation independently with respect to each other and conjointly with each other about the common axis. The first carrier preferably overlies the second carrier and is coupled to its associated motor by a shaft that extends along the common axis. The second carrier preferably is coupled to its associated motor by a sleeve that surrounds the shaft.

Each carrier preferably comprises a central hub coupled to its associated motor and a peripheral portion on which the fingers are mounted. The peripheral portion of each carrier preferably includes an annular rim coupled to the associated hub and a plurality of ring segments removably mounted on the annular rim by quick-release locks. The ring segments have radially outwardly extending legs on which the fingers are mounted, with the legs on the first carrier being interdigitally disposed between the legs on the second carrier so that the fingers of each pair are angularly spaced from each other. The fingers of one array are mounted in fixed position on the associated carrier, while the fingers of the other array are resiliently biased toward the fingers of the one array for accommodating size variations among the articles of glassware. A layer of resilient material preferably is disposed on the glassware-engaging surface of each finger for resiliently engaging the glassware articles while reducing slippage of or damage to the articles.

A drive roller in the preferred embodiment of the invention is disposed for engaging and rotating an article of glassware at at least one of the stations, and a support pad and support roller are disposed at the station for supporting the article of glassware during rotation. A pair of angularly spaced back-up rollers are disposed adjacent to the support pad for holding the article in position while the article is rotated by the drive roller. The back-up rollers may be mounted for adjustment with respect to each other and with respect to the axis of rotation of the carriers for accommodating glassware articles of differing sizes. As an alternative, the back-up rollers maybe mounted in fixed position on a roller support base, which may be replaceable for accommodating containers of differing diameter. The drive roller is coupled to an associated electric motor, and preferably is selectively pivotable into and out of engagement with a glassware article at the associated station.

A method of transporting glassware through a series of stations in accordance with a presently preferred embodiment of the invention contemplates providing first and second circumferential arrays of alternately opposed glassware gripping fingers, moving at least one of the arrays toward the other for simultaneously gripping articles of glassware at the stations, rotating the first and second arrays simultaneously on a common axis to index glassware between the stations, and then moving at least one of the arrays away from the other to release the articles of glassware at the stations. The stations preferably are disposed at equal angular increments around the common axis of rotation, and the steps of gripping, rotating and releasing the articles are repeated incrementally to convey the articles through the stations. An infeed conveyor preferably is located at one of the stations, and an outfeed conveyor is located at another of the stations for transporting containers to and from the apparatus of the invention. At at least one of the stations, each article of glassware in turn is inspected for commercial variations or for mold of origin.

BRIEF DESCRIPTION OF THE DRAWINGS

The invention, together with additional objects, features and advantages thereof, will be best understood from the following description, the appended claims and the accompanying drawings in which:

FIG. 6 is a perspective view of a ring segment subassembly in the carrier of FIG. 5;

FIG. 7 is a perspective view of a finger assembly in the carrier of FIGS. 5 and 6;

FIG. 17 is an exterior perspective view of the drive roller mounting arrangement illustrated in FIG. 14;

FIG. 18 is an interior perspective view of the drive roller mounting arrangement illustrated in FIG. 17;

DETAILED DESCRIPTION OF PREFERRED EMBODIMENTS

Figure 13:
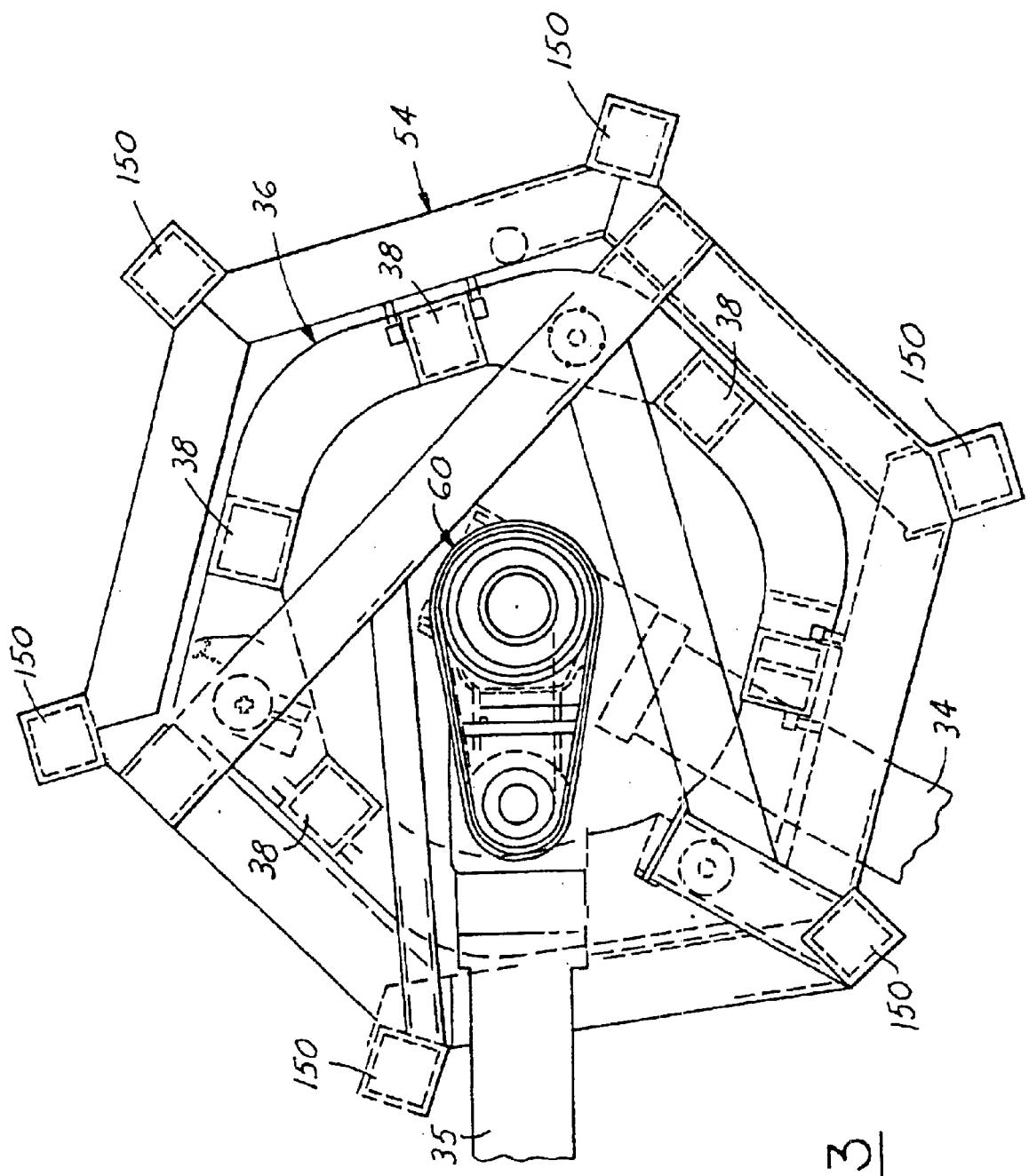
FIG. 13 is a top plan view of the frame and base assembly illustrated in FIG. 12.

The drawings illustrate an apparatus 30 in accordance with a presently preferred embodiment of the invention for indexing articles of glassware 32, such as glass containers, through a series of stations. These stations preferably are spaced at equal angular increments around a common axis. An infeed conveyor 34, such as an endless belt conveyor, brings containers 32 in sequence to one of the stations. In general, apparatus 30 grips containers 32 as they are presented on infeed conveyor 34, and incrementally transports containers 32 to each station in turn around the apparatus. At at least some of the stations, containers 32 are held in position and rotated about their axes for inspection or other purposes. The containers 32 are ultimately indexed to an outfeed conveyor 35 (FIGS. 13 and 24), to a cullet or reject chute or conveyor for removing containers that did not pass inspection, or to a sampling conveyor or other device for sampling containers from a specific mold, for example. In the preferred implementation of the invention, the containers are subject to inspection for commercial variations at at least some of the stations. Such inspection preferably comprises electro-optical inspection of container dimensional or other characteristics, such as shown in U.S. Pat. No. 2,682,802 (finish check detection), U.S. Pat. Nos. 3,880,750, 5,896,195 or EP 0961113 (sealing surface inspection), U.S. Pat. Nos. 4,378,493, 4,378,495, 4,584,469, 5,233,186, 5,291,271 or 5,637,864 (container sidewall inspection), or EP 0764846 (container bottom inspection). Successive containers can also be inspected to determine or read the code molded into the container for indicating container mold of origin, as illustrated for example in U.S. Pat. No. 4,644,151. Although electro-optical inspection techniques are currently preferred, the apparatus of the invention can also accommodate mechanical inspection techniques, such as illustrated in U.S. Pat. No. 5,414,939, in which the container is contacted by one or more rollers or fingers as it is rotated about its axis. Electrical inspection techniques, as illustrated in U.S. Pat. No. 4,046,258, are also envisioned.

Figure 14:
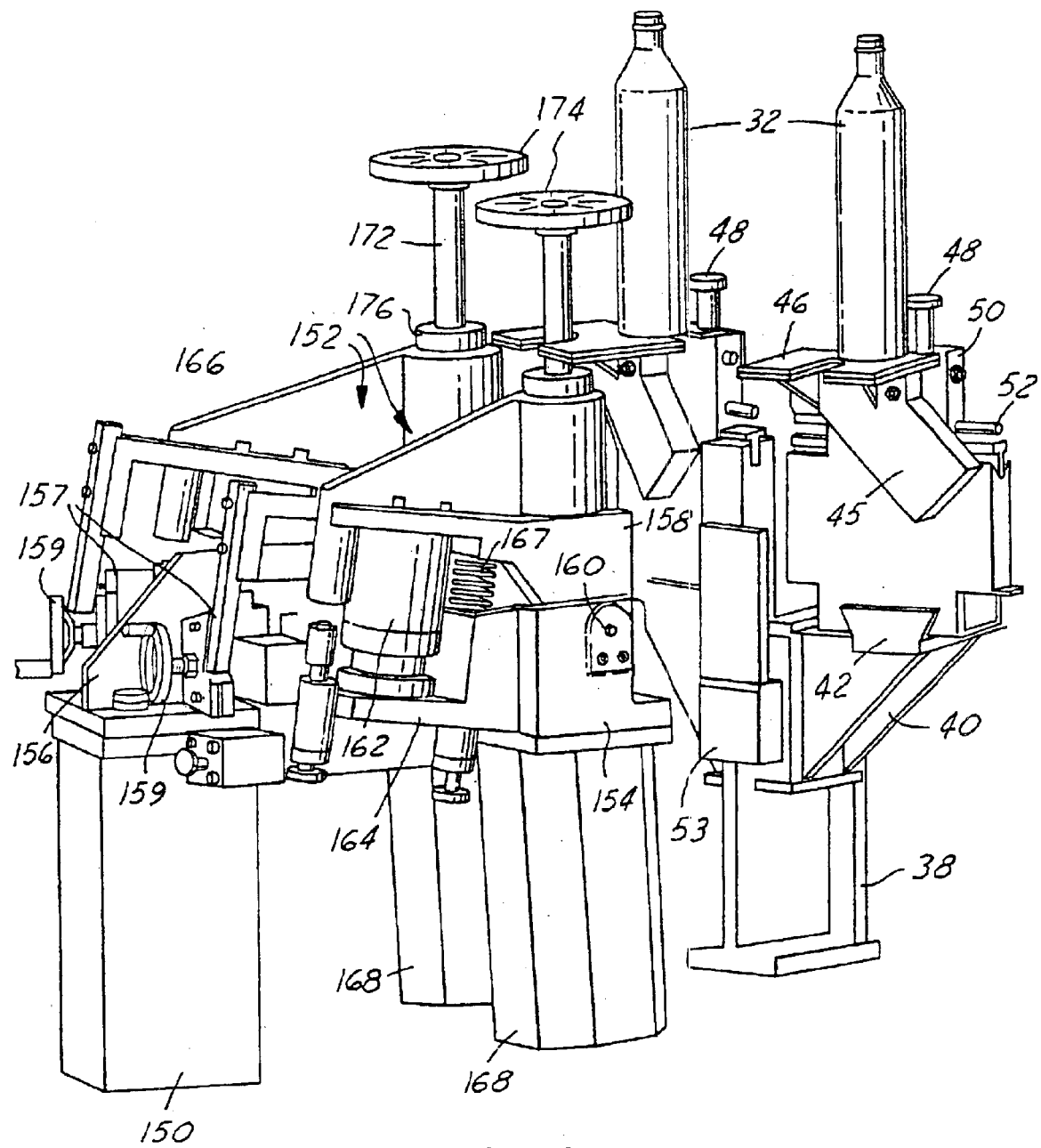
FIG. 14 is a fragmentary radially exterior perspective view of a roller drive motor mounting arrangement illustrated in FIGS. 1 and 2.
Figure 16:
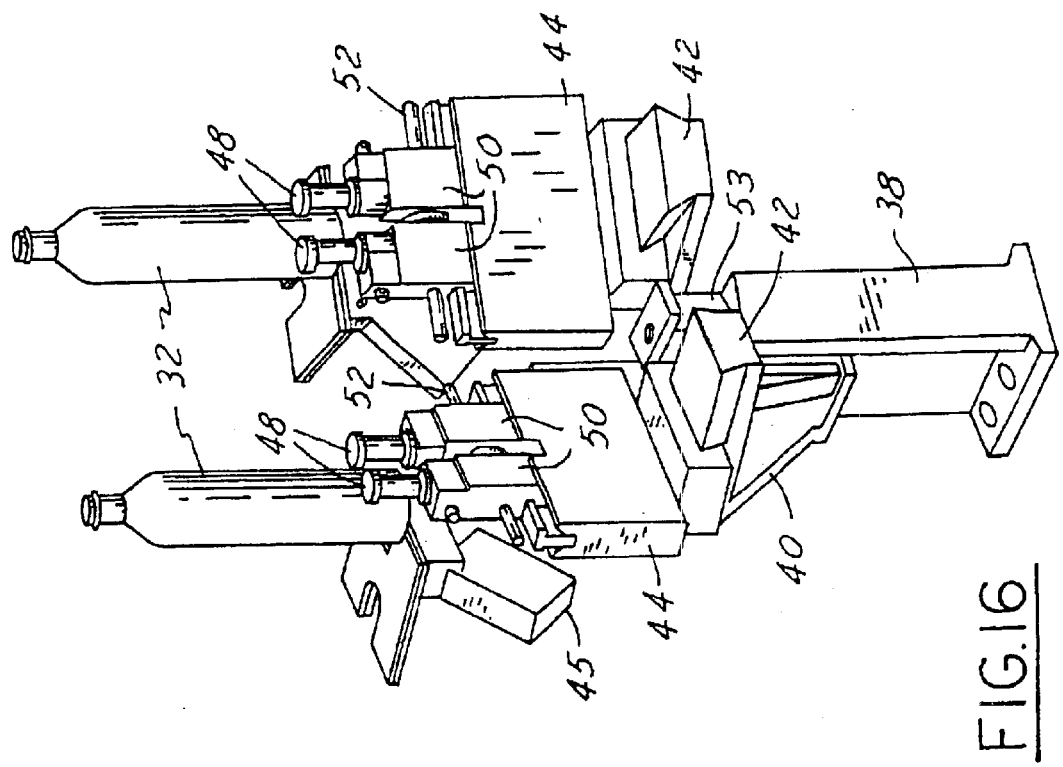
FIG. 16 is a radially interior perspective view of the apparatus as illustrated in FIG. 15.
Figure 15:
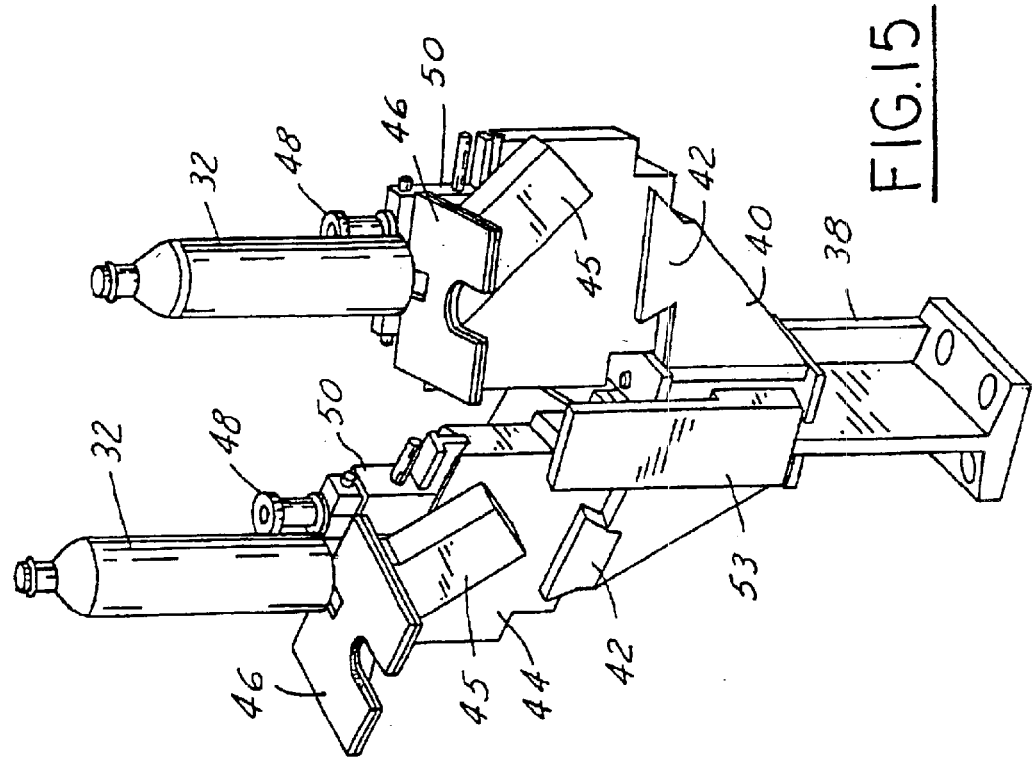
FIG. 15 is a fragmentary radially exterior perspective view of the glassware support pads and back-up rollers at two stations of the apparatus of FIGS. 1 and 2.
Figure 20:
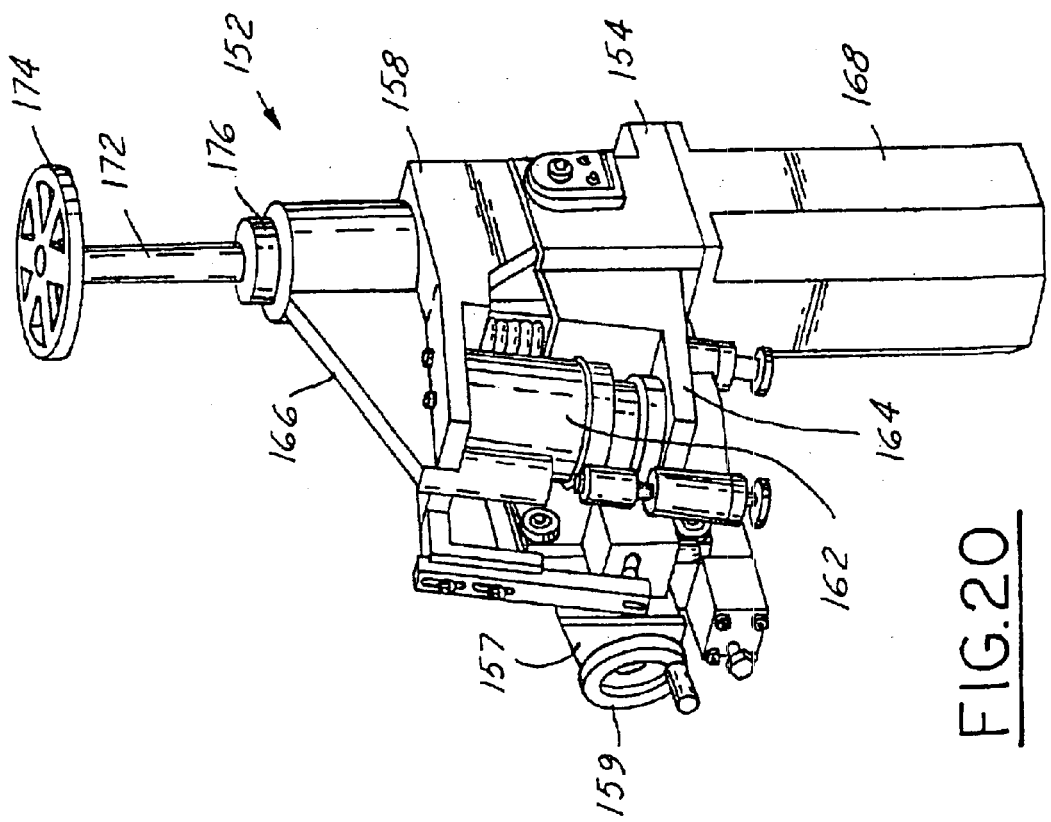
FIGS. 19 and 20 are interior and exterior perspective views of one of the drive roller subassemblies in FIGS. 17 and 18.
Figure 19:
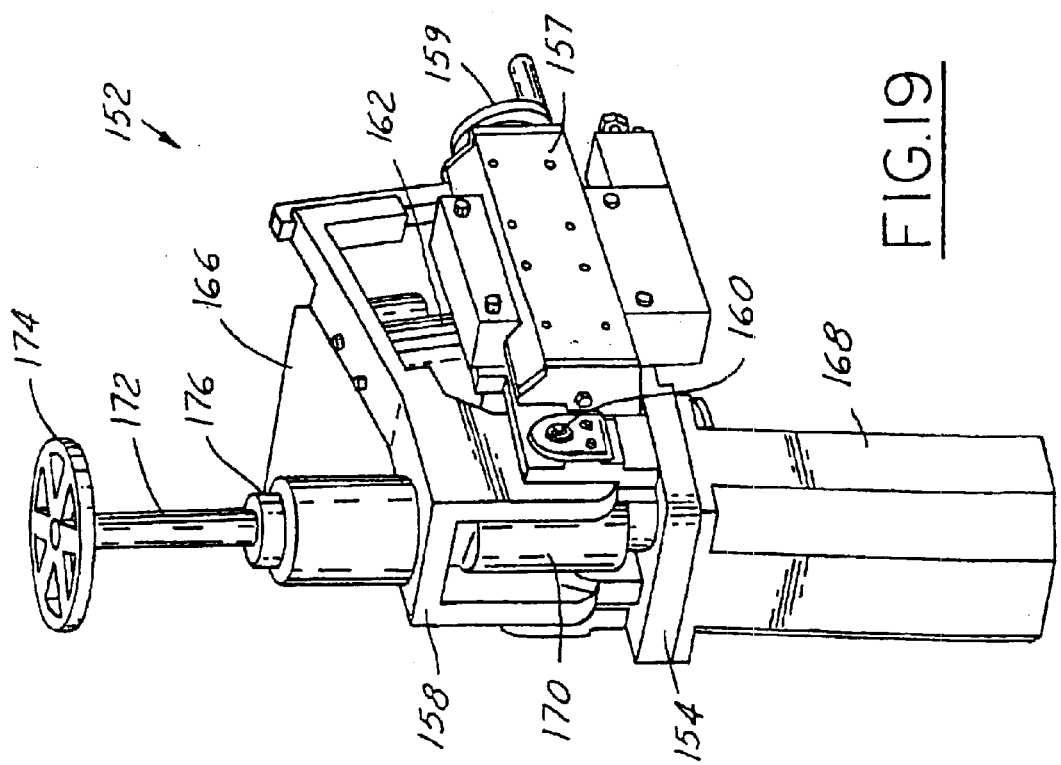

Referring to the drawings, apparatus 30 includes a base 36 (FIGS. 1, 12 and 13) of heavy construction. A circumferential array of angularly spaced support posts 38 are disposed around the periphery of base 36 and extend upwardly therefrom. Each support post terminates at its upper end in a Y-shaped support bracket 40 (FIG. 15) on which a spaced pair of radially oriented horizontal slides 42 are mounted (FIG. 15). A support 44 is mounted on each slide 42, and a slide pad 46 is mounted by a bracket 45 at the upper end of each support 44. Posts 38 are distributed around the periphery of base 36, and Y-bracket 40 is designed such that slide pads 46 are at equal angular increments around the central axis of apparatus 30. A roller 47 (FIG. 22) is mounted for rotation about a horizontal radial axis beneath each pad 46, and has a surface that extends through a slot in pad 46 for engaging the bottom of a container and supporting the container for rotation about its axis. A pair of free wheeling rollers 48 are carried on associated slides 50 at the upper end of each support 44 (FIGS. 14–16). Slides 50 are slidably mounted on supports 44 such that rollers 48 are adjustable with respect to each other laterally of the axis of apparatus 30. Rollers 48 are disposed above the plane of pad 46 for providing back-up support to containers 32 on pads 46, as will be described. Slides 50 are secured to a rod 52 that is mounted on pad support bracket 45. Pads 46 are thus at equal angular spacing around the central axis of the apparatus and at identical vertical elevation. The positions of pads 46 are adjustable radially of the apparatus axis by means of slides 42, and rollers 48 are adjustable laterally to accommodate containers of differing sizes. As an alternative, rollers 48 may be fixedly disposed on a support 44a (FIG. 22), which is itself replaceable for accommodating containers of differing diameter. Y-bracket 40 is mounted on post 38 by a vertical dovetail slide 53 for adjusting vertical positions of pads 46.

Figure 3:
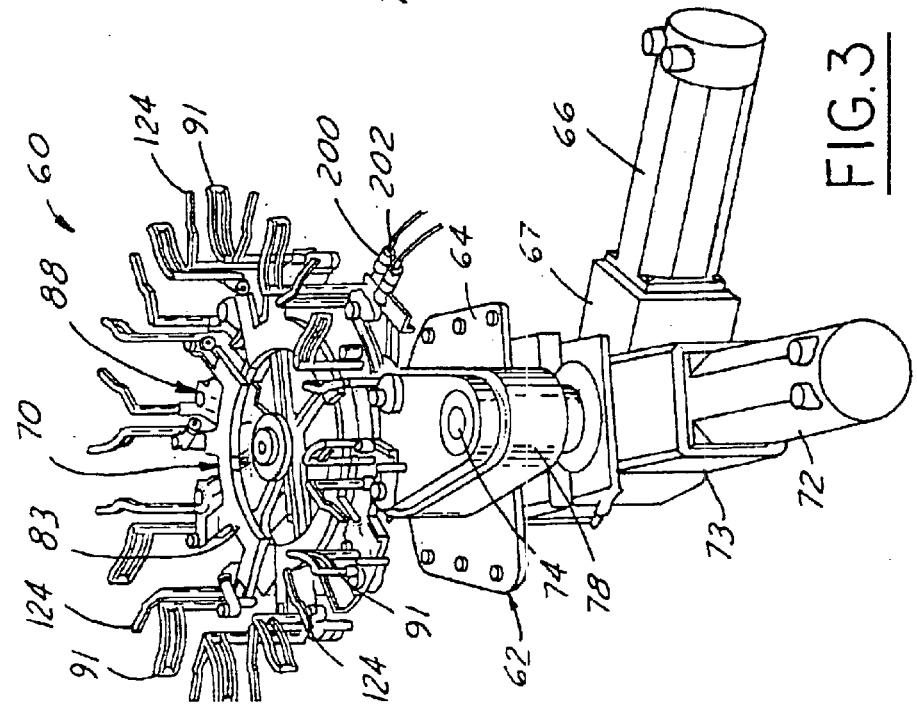
FIG. 3 is a perspective view of the carrier drive unit subassembly in the apparatus of FIGS. 1 and 2.
Figure 11:
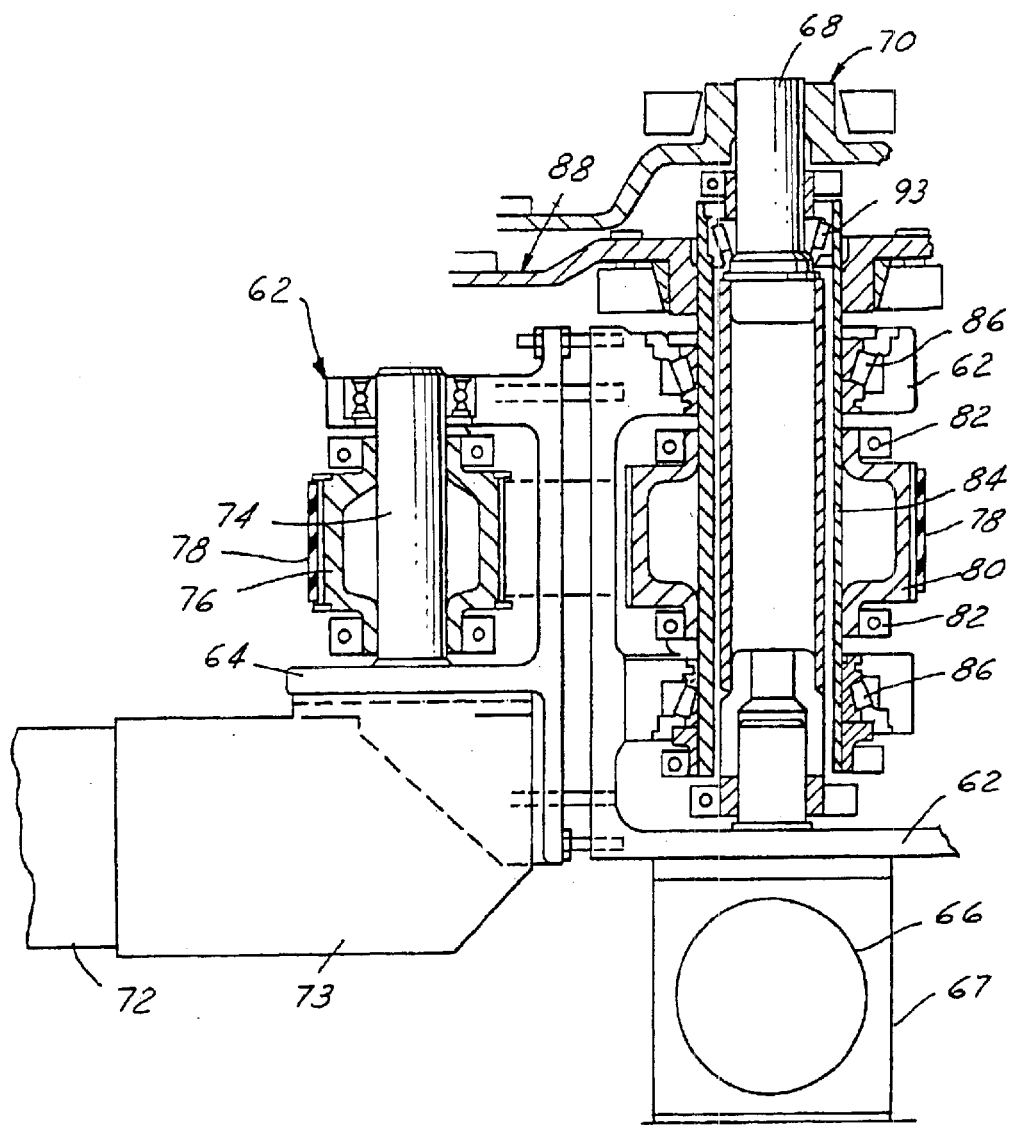
FIG. 11 is a fragmentary sectional view diametrically bisecting the carrier assembly of FIGS. 3 and 4 and illustrating interconnection of the carriers to the drive motors.
Figure 12:
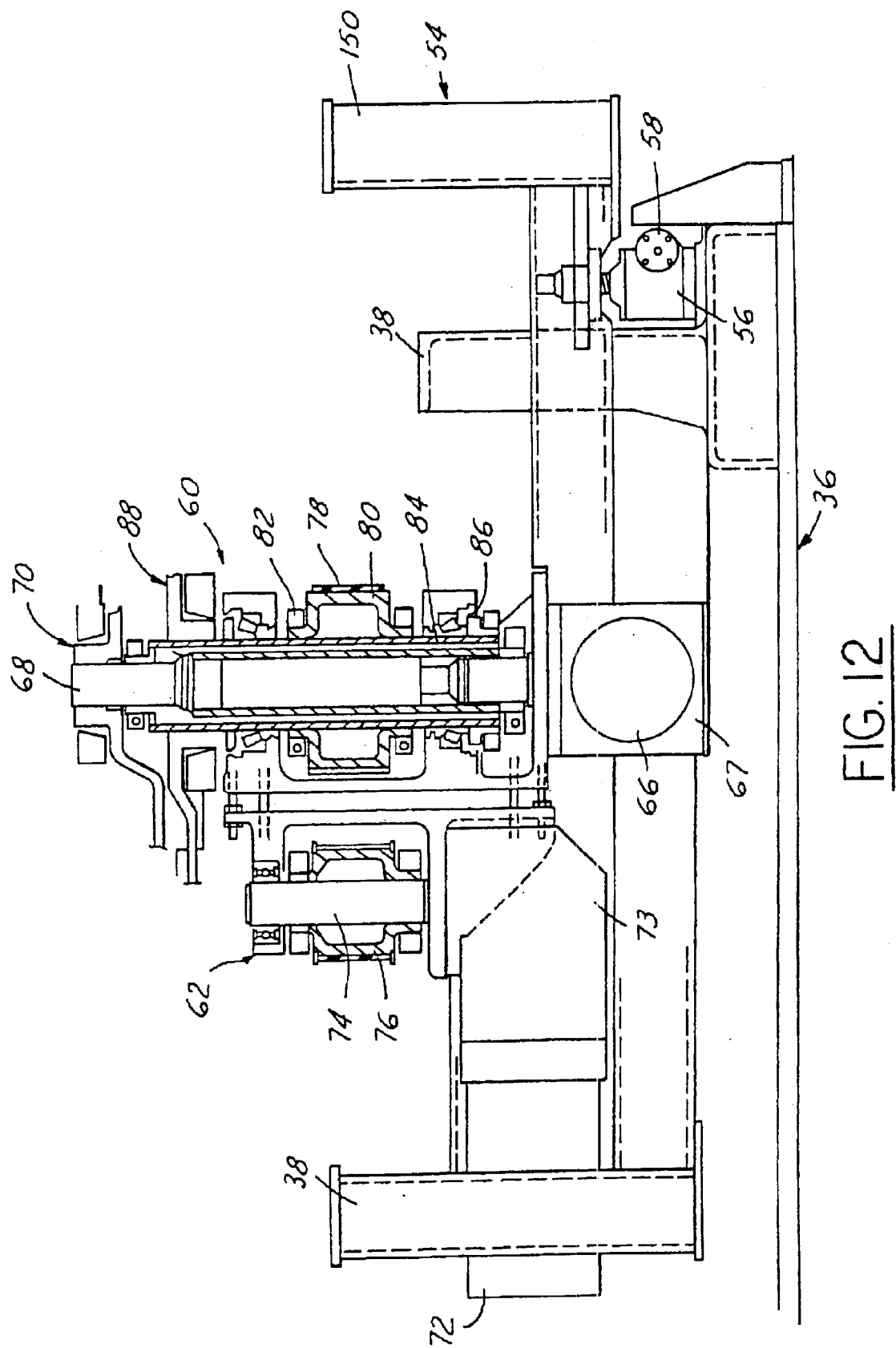
FIG. 12 is a fragmentary sectional view similar to that of FIG. 11 but showing the drive roller and carrier subassembly frame movably mounted on the support base of the apparatus.

A lift frame 54 (FIGS. 1, 12 and 13) is mounted on base 36 and is coupled to a linear actuator 56 driven by a rotary electric servo motor 58 (FIG. 12) for controlled vertical motion of frame 54 with respect to base 36. A carrier drive unit or subassembly 60 is mounted on lift frame 54. Carrier drive unit 60 includes a central support 62 (FIGS. 3, 11 and 12) that is mounted on frame 54 (FIG. 12). A first rotary electric servo motor 66 and an associated gearbox 67 are mounted on the underside of support 62, and are coupled to a shaft 68 that extends upwardly through support 62. The axis of rotation of shaft 68 defines the central axis of carrier drive unit 60 and apparatus 30. The upper end of shaft 68 is coupled to a first or upper carrier 70. A second rotary electric servo motor 72 and as associated gearbox 73 are mounted beneath a flange 64 on support 62 laterally offset from the axis of shaft 68. A shaft 74 extends upwardly from motor 72 and gearbox 73 parallel to shaft 68, and is coupled by a pulley 76 and a cogged timing belt 78 to a pulley 80 concentrically surrounding shaft 68. Pulley 80 is secured by clamp rings 82 to a sleeve 84 that is mounted by roller bearings 86 for rotation around shaft 68. The upper end of sleeve 84 is coupled to a second or lower carrier 88. The outer races of roller bearings 86 are secured to support 62. Shaft 68 is supported within sleeve 84 by a roller bearing 93. Thus, first or upper carrier 70 is rotatable about the axis of shaft 68 under control of motor 66 and gearbox 67, while second or lower carrier 88 is rotatable about the axis of shaft 68 (the central axis of apparatus 30) under control of motor 72 and gearbox 73 and independently of rotation of upper carrier 70.

Upper carrier 70 (FIGS. 4–7) includes a carrier base 73 having a central hub 75 and an annular rim 77 coupled to hub 75 by a plurality of circumferentially spaced radially extending spokes 79. Three ring segments or subassemblies 83 are secured around the periphery of rim 77, each by a pair of angularly spaced tapered dovetails 81 and a quick-turn cam clamp 85. Each ring segment 83 comprises an arcuate base 87 from which a plurality (preferably four) angularly spaced legs 89 extend radially outwardly. In the preferred embodiment illustrated in the drawings, there are three ring segments 83, each having four radially extending legs 89 that are spaced from each other in equal angular increments both within each segment 83 and among segments 83. A container-gripping finger assembly 91 is secured to the outer end of each leg 89. Each assembly 91 comprises an inverted L-shaped finger 90 having a vertical leg 92 and a pair of spaced parallel horizontal legs 94 interconnected at their outer ends by a bridge 96. Leg 92 is received within a leg housing 98 and is removably secured within the housing by a spring-loaded lock pin 100. Housing 98 is secured by screws 102 to ring segment leg 89 (FIGS. 5 and 6) such that finger assembly 90 extends upwardly therefrom. A layer or coating of resilient elastic material such as polyurethane is provided on the inside surface of each leg 94 adjacent to the radially outer end thereof for engaging containers without damage to the containers and to enhance frictional gripping of the containers, as will be described. In the preferred embodiment, finger legs 92 are non-rotatable withing housings 98.

Second or lower carrier 88 (FIGS. 4 and 8–10) includes a base 106 having a central hub 108 and an annular rim 110 interconnected by a plurality of radially extending spokes 112. A plurality of ring segments or subassemblies 114 are mounted around the periphery of rim 110 by angularly spaced tapered dovetails 116 and quick-turn cam clamps 118. Each ring segment 114 includes an arcuate base 120 from which a plurality (preferably four) legs 122 extend radially outwardly. A spring finger assembly 124 is mounted at the outer end of each ring segment leg 122. Each spring finger assembly 124 comprises an inverted L-shaped finger 126 having a vertical leg 128 and a radially outwardly extending horizontal leg 130. A resilient elastic layer or coating 132 is provided on the inside surface of each leg 130 adjacent to the outer end thereof for enhanced frictional gripping of containers without damage to the containers, as will be described. Each vertical leg 128 is received within a housing 134 and non-rotatably removably held within the housing by a spring-loaded lock pin 136. Housing 134 is rotatably mounted on a base 138. Housing 134 and base 138 have opposed arms 140, 142, between which a coil spring 144 is captured in compression. Coil spring 144 thus biases finger legs 130 clockwise in FIGS. 4 and 8–10, to accommodate tolerance variations in container diameter.

Figure 4:
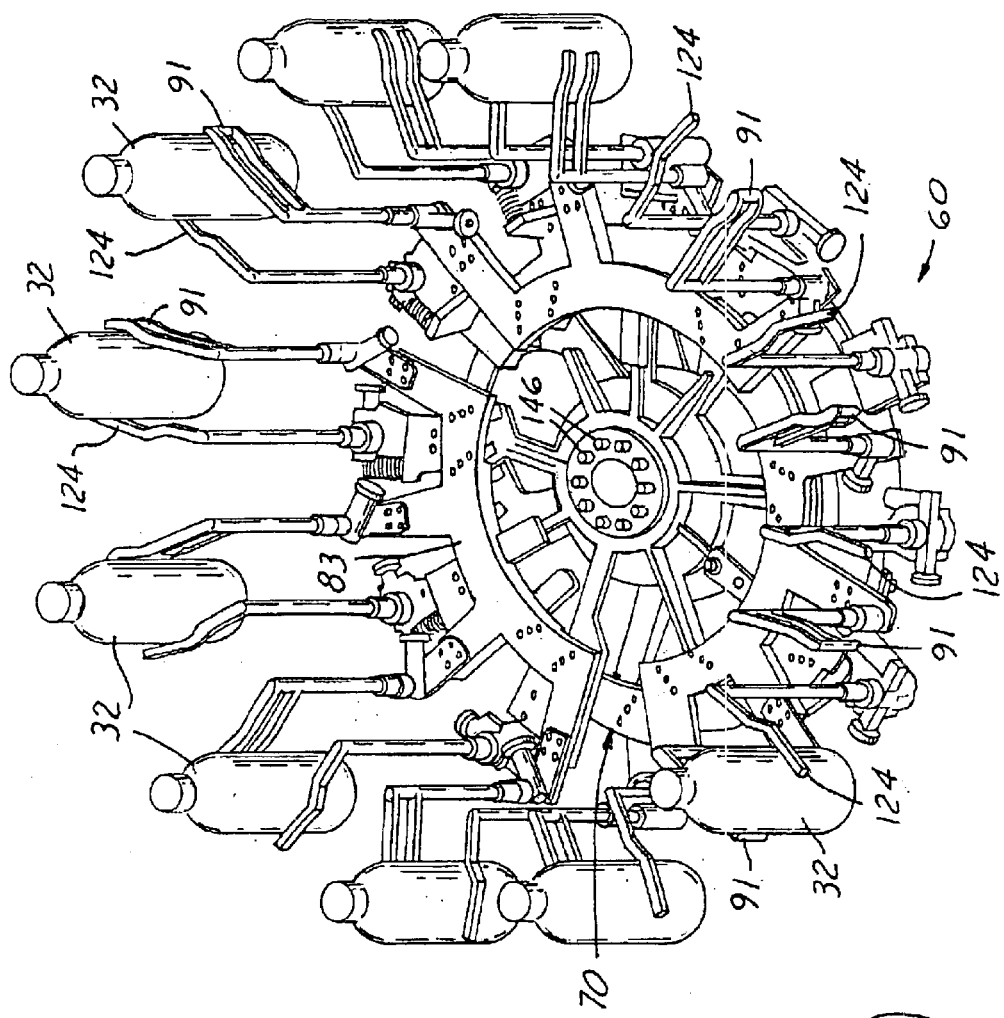
FIG. 4 is a fragmentary perspective view of the carrier assembly of FIG. 3 gripping containers for purposes of transport between stations.
Figure 5:
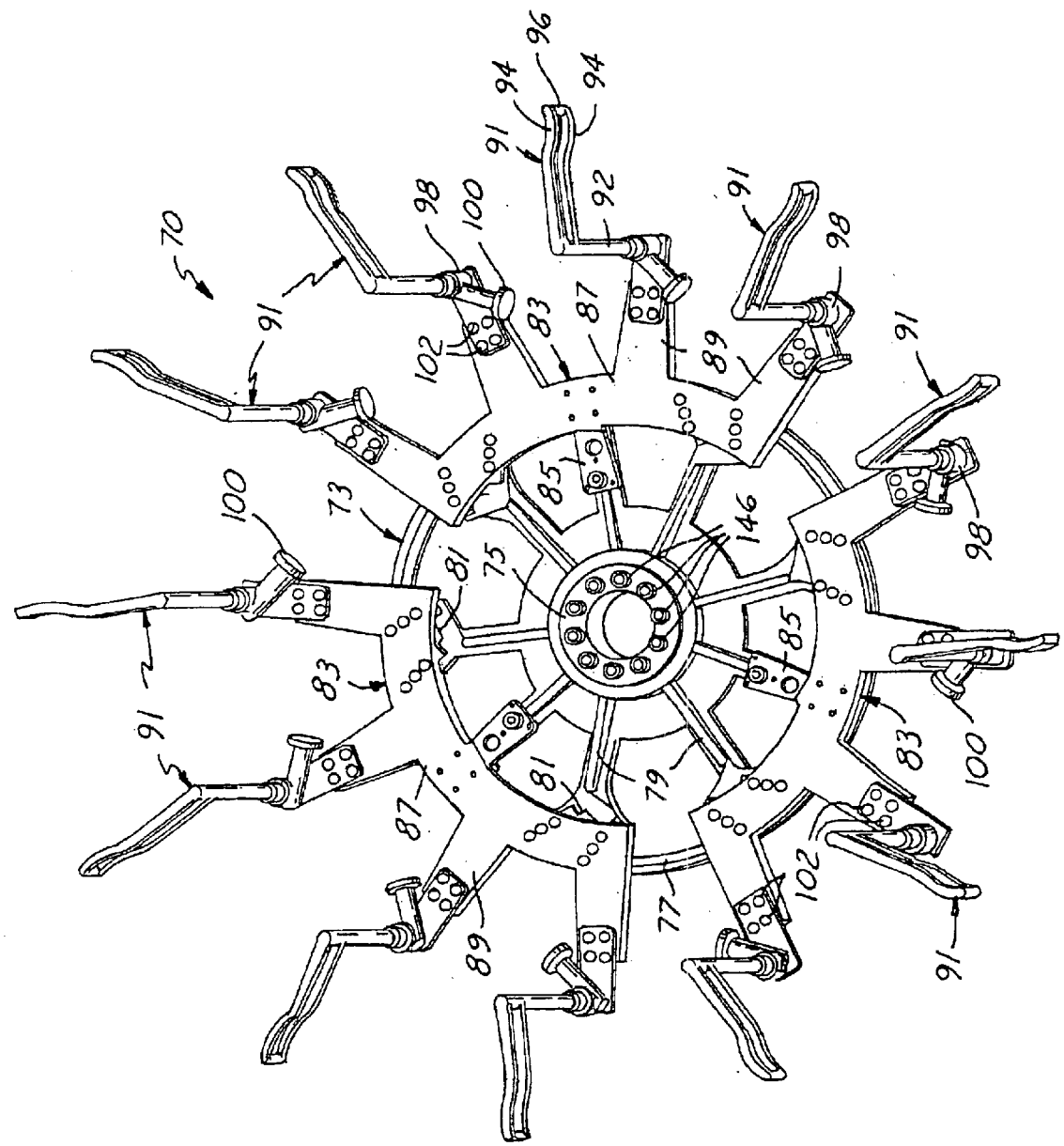
FIG. 5 is a perspective view of a first or upper carrier in the assembly of FIGS. 3 and 4.
Figure 8:
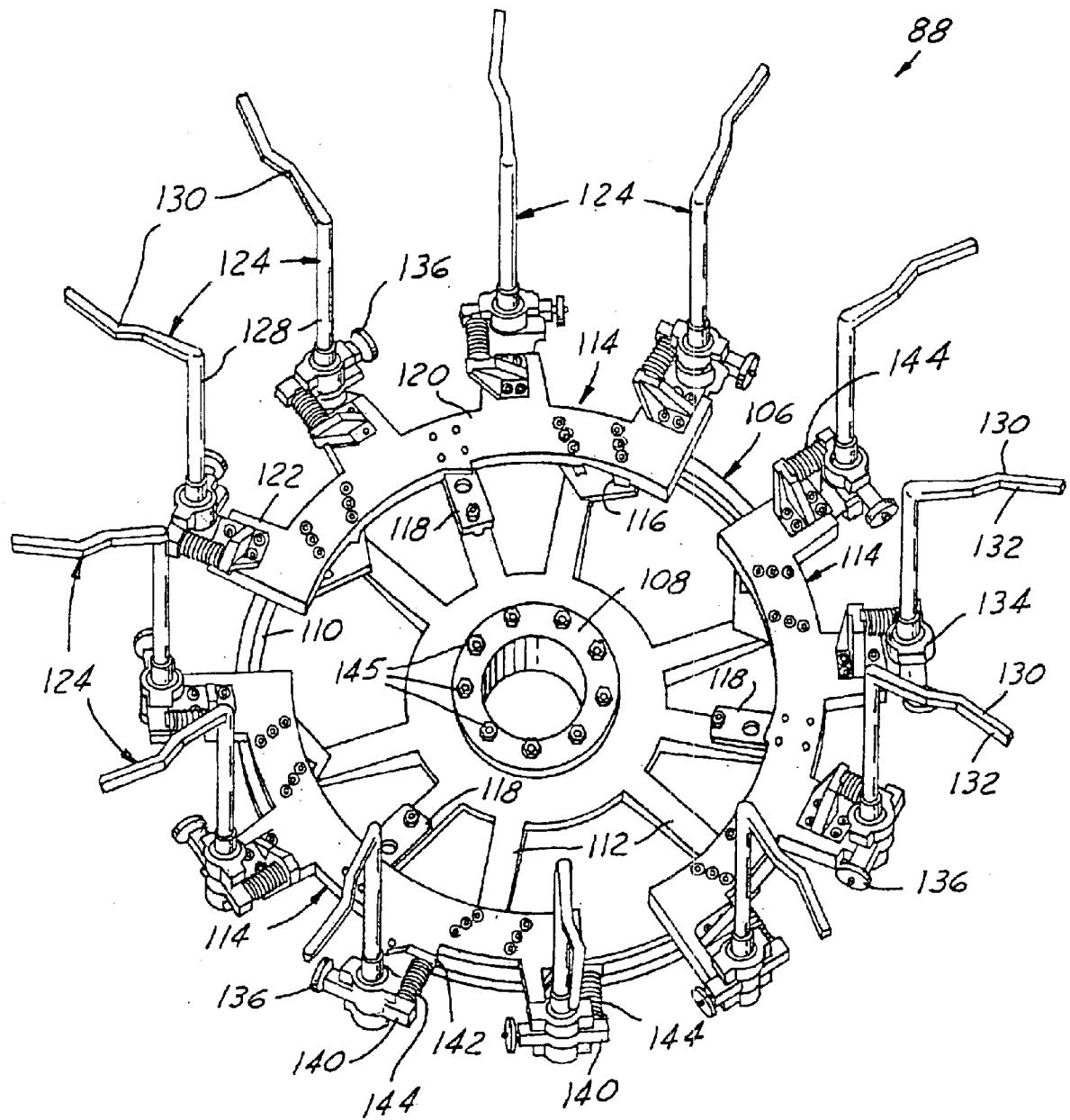
FIG. 8 is a perspective view of the second or lower carrier in the carrier assembly of FIGS. 3 and 4.
Figure 9:
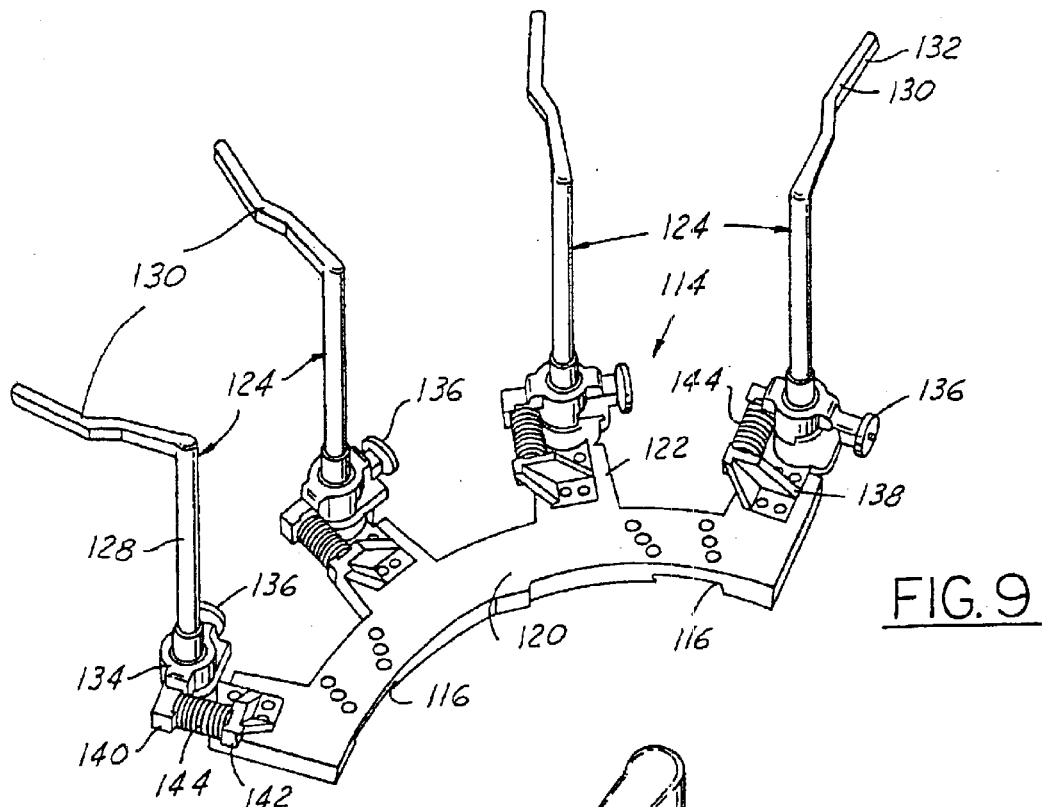
FIG. 9 is a perspective view of a ring segment subassembly in the carrier of FIG. 8.
Figure 10:
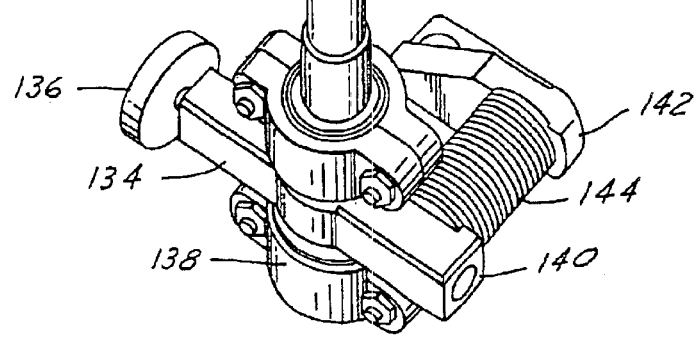
FIG. 10 is a perspective view of a finger assembly in the carrier of FIGS. 8 and 9.

In assembly, lower carrier 88 is secured to sleeve 84 (FIGS. 11 and 12) such as by fasteners 145 (FIG. 8), and upper carrier 70 is secured to shaft 68 by fasteners 146 (FIGS. 4 and 5) overlying lower carrier 88. The hubs of the respective carriers are secured to sleeve 84 and shaft 68 such that finger assemblies 91 of upper carrier 70 and finger assemblies 124 of lower carrier 88 are interdigitally staggered, as best seen in FIG. 4. Fingers 90 of upper carrier 70 and fingers 126 of lower carrier 88 are dimensioned and adjusted such that each horizontal leg 130 of a finger 126 is disposed vertically between horizontal legs 94 of the opposing finger 90. This promotes stability of containers during transport by the carriers. Elastomeric coatings or layers 104, 132 are circumferentially opposed to each other. The upper and lower carriers thus form a plurality of finger pairs that cooperate with each other, as will be described, to grip and transport containers under control of carrier drive motors 66, 72. These finger pairs are disposed at equal angular increments around the periphery of the carriers. These angular increments are equal in number to and equal in spacing between the stations defined by container support pads 46 and the infeed, outfeed and cullet stations of apparatus 30.

Referring to FIGS. 1–2, 12–14 and 17–18, lift frame 54 includes a peripheral array of support posts 150. A pair of drive roller assemblies 152 are mounted on the upper end of at least some of the support posts 150. Each drive roller assembly 152 comprises a fixed support bracket 154 (FIGS. 17–18) secured by an L-bracket 156 to the upper end of support post 150, and a pivotal support bracket 158 mounted within fixed bracket 154 by a pivot 160. Each fixed bracket 154 is coupled to L-bracket 156 by a dovetail slide 157 and a hand wheel 159 for adjusting the radial position of roller assembly 152. A linear actuator 162, such as a voice coil actuator, is mounted between arms 164, 166 of fixed bracket 154 and pivotal bracket 158 respectively. A coil spring 167 is also captured in compression between bracket arms 164, 166 in parallel with linear actuator 162. Coil spring 167 thus urges pivotal bracket 158 and drive roller 174 into radial engagement with containers 32 at the inspection stations, which spring force must be overcome by actuator 162. A rotary electric servo motor 168 is suspended beneath each fixed bracket 154, and is connected by a flexible coupling 170 to a roller drive shaft 172. A container drive roller 174 is secured to the upper end-of each shaft 172, which is rotatably mounted on pivotal bracket 158 by a bearing 176.

A pair of circumferentially spaced rollers 180 (FIG. 1) are mounted on a fixed support bracket 182 above at least some of the support pads 46 for engaging and radially supporting the neck or finish of containers 32 as the containers are rotated by drive roller 174.

Figure 21:
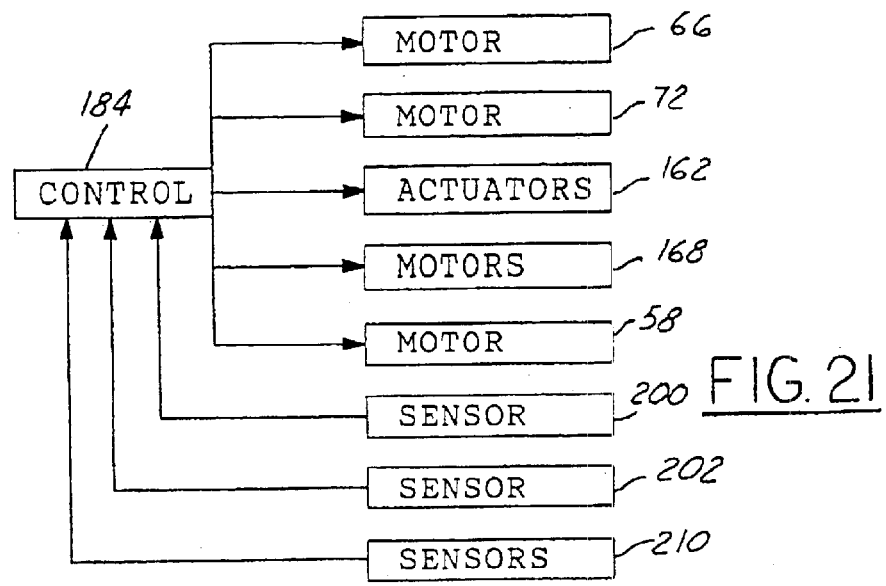
FIG. 21 is a functional block diagram of the motor and actuator control electronics for the apparatus of FIGS. 1–20.
Figure 25:
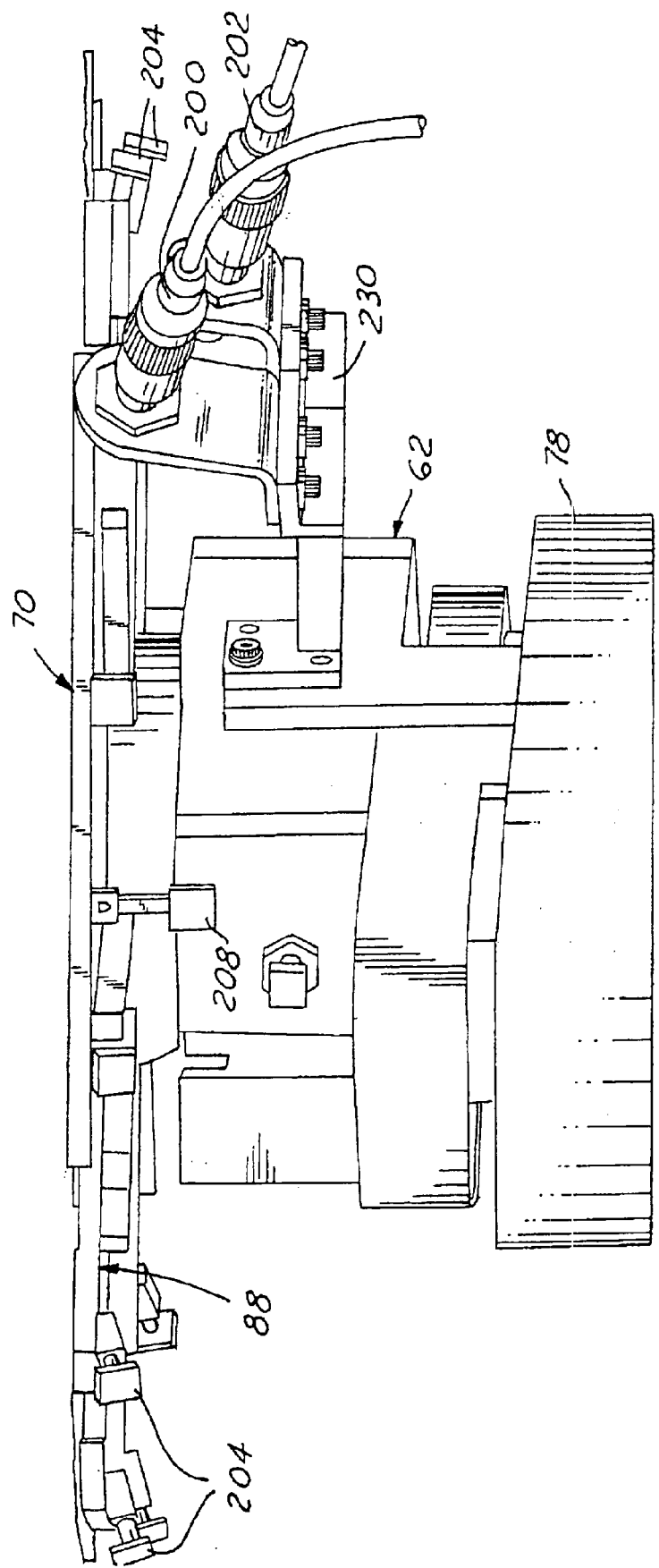
FIG. 25 is a fragmentary elevational view of carrier drive unit illustrating the carriage position sensors.
Figure 26:
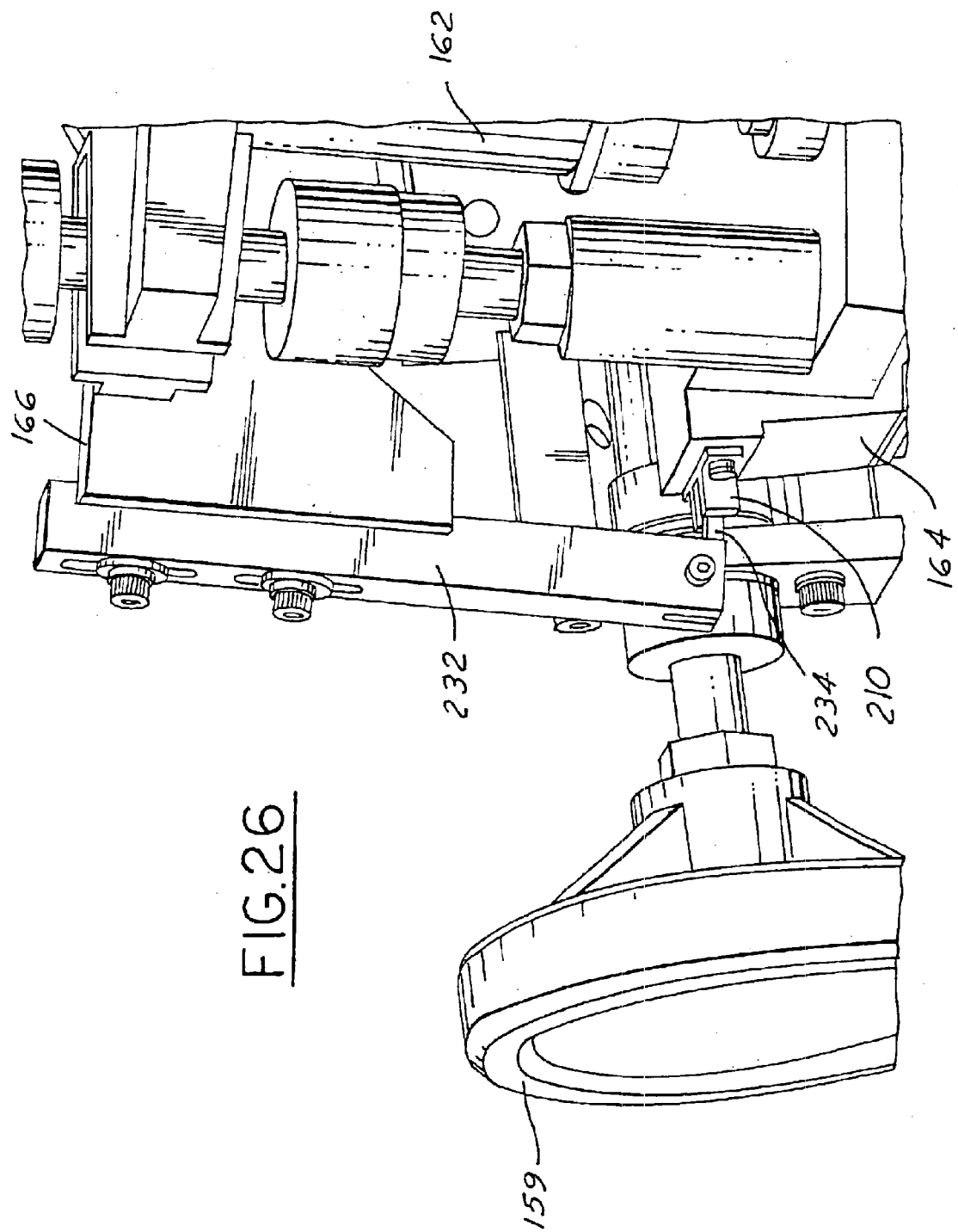
FIG. 26 is a fragmentary extension perspective view of a drive roller subassembly.

A pair of proximity sensors 200, 202 (FIGS. 1, 3 and 21) are disposed in fixed position adjacent to the periphery of lower carrier 88. Sensor 200 is responsive to an array of circumferentially spaced fingers or tabs 204 (FIG. 25) on lower carrier 88 to define angularly spaced home positions for lower carrier 88 at each inspection station. Sensor 202 is responsive to a finger 208 (FIG. 25) on lower carrier 88 to reset the machine controller upon each revolution of lower carrier 88. Sensors 200, 202 are mounted in fixed position on a bracket 230 (FIG. 25) secured to central support 62, and thus form part of carrier drive unit 60. Thus, the machine control electronics 184 (FIG. 21) tracks position of lower carrier 88. FIG. 21 illustrates control electronics 184 having outputs connected to upper carriage drive motor 66, lower carriage drive motor 72, drive roller actuators 162, drive roller motors 168 and lift frame motor 58. A switch 185 on base 36 (FIG. 1) is responsive to an arm 186 extending from frames 54 to sense that the frame is in the fully lowered position. Proximity sensors 200, 202 also provide input to control electronics 184. An optical sensor 210 (FIG. 26) is mounted on each drive roller fixed bracket arm 164. A flag 234 is carried at the lower end of each leg 232 for receipt in the associated position sensor 210. Each sensor 210 indicates to control electronics 184 whether the associated drive roller assembly is in the forward position for engaging a container at the associated inspection station, at which the associated flag 234 is clear of the associated sensor 210, or in the retracted position at which the associated flag engages the associated sensor.

Figure 24:
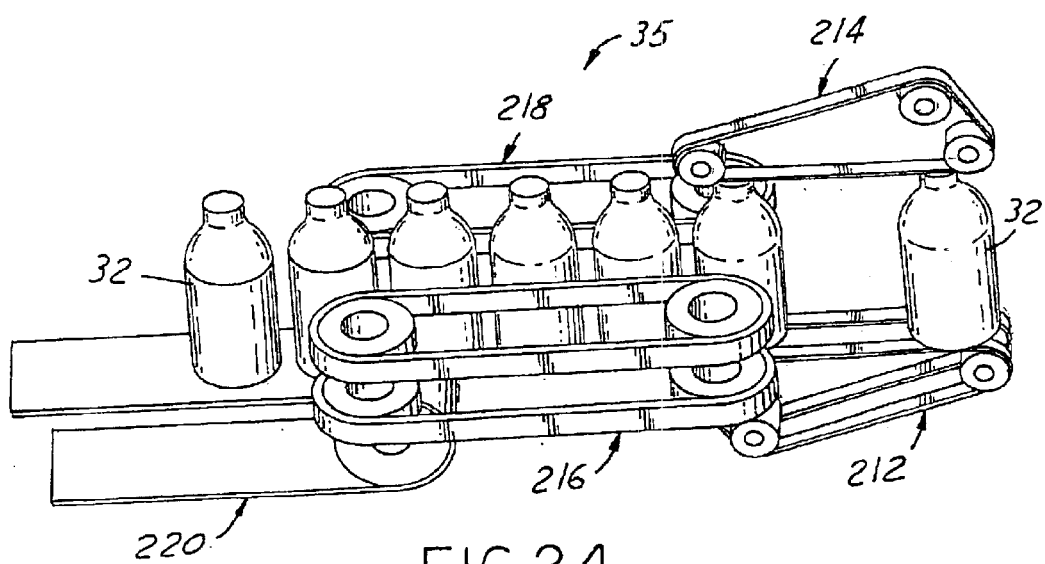
FIG. 24 is a fragmentary perspective view of the container out-feed conveyor in the apparatus of FIG. 1.

FIG. 24 illustrates outfeed conveyor 35 in greater detail. A lower endless belt conveyor 212 and an upper endless belt conveyor 214 are disposed to engage the lower and upper surfaces of a container 32 deposited at the outfeed station by apparatus 30. Conveyors 212, 214 rapidly move containers away 32 from the periphery of apparatus 30 to a position between a pair of laterally opposed endless belt conveyors 216, 218. Conveyors 216, 218 convey containers 32 radially outwardly of apparatus 30 to an endless belt conveyor 220, which transports containers 32 for further processing. An air jet or the like may be disposed adjacent to an edge of conveyor 220 and coupled to control electronics 184 (FIG. 21) for removing from conveyor 220 any containers that do not pass inspection. Conveyor 214, which engages the sealing surface of containers 32 in the embodiment illustrated in FIG. 24, may be replaced by laterally opposed conveyors that do not engage the container sealing surface where such feature is desired by a customer. Use of an outfeed conveyor 35, such as that illustrated in FIG. 24, is preferred for rapidly moving containers 32 away from the periphery of apparatus 30, and thereby facilitating high-speed inspection of containers as on the order of three hundred containers per minute.

In operation, carriers 70, 88 cooperate with each other, under the control of motors 66, 72 and control electronics 184 (FIG. 21) to transport sequential containers 32 from infeed conveyor 34 through sequential stations to outfeed conveyor 35. The illustrated embodiment of the invention has twelve pairs of fingers 91, 124 carried by the carriers, and is thus a twelve station apparatus. The first station is at the infeed end of conveyor 34, and the last station would typically be at the end of outfeed conveyor 35. The ten remaining stations preferably are occupied by suitable container inspection devices and systems, such as those illustrated in the several above-noted patents. These inspection systems are not illustrated in the application drawings to facilitate understanding of the transport apparatus that characterizes the present invention. In use, one or more of the inspection stations may be empty, or the inspection system at that station may be wholly or partially deactivated. Vertical positions of frame 54 and rollers 48 are adjusted as a function of container height. Horizontal positions of rollers 48 and drive roller assemblies 152 are adjusted as a function of container diameter.

Motors 66, 72 coupled to carriers 70, 88 are first actuated by control electronics 184 (FIG. 21) to rotate one or both of the carriers toward each other (i.e., counterclockwise for upper carrier 70 and clockwise for lower carrier 88) so as to move fingers 90, 126 toward each other and grip containers 32 at each station between the fingers. In the presently preferred embodiment of the invention illustrated in the drawings, it has been found to be advantageous to rotate lower carrier 88, containing the upstream or leading fingers 124, over a greater angular dimension than upper carrier 70 carrying the downstream or trailing fingers 91 when gripping or releasing the containers at the inspection stations. Thus, the angular extent of rotation of the carriers during gripping and releasing of the containers need not be identical, and indeed one of the carriers, in this case the carrier containing the trailing fingers 91, need not be rotated at all. The torque applied to carrier 88 is monitored by monitoring current applied to motor 72. When this torque exceeds a preset level, rotation of the carrier is terminated. When gripping the containers, fingers 124 push containers 32 against fingers 91. The containers roll along the opposing surface of fingers 91 until nested in position at the radial extremity of the fingers and gripped by opposing fingers 124. Resilient layers 104, 132 on fingers 90, 126 facilitate frictional gripping of the containers and reduce damage to the containers. Coil springs 144 associated with fingers 126 accommodate tolerance variations among the containers.

Figure 1:
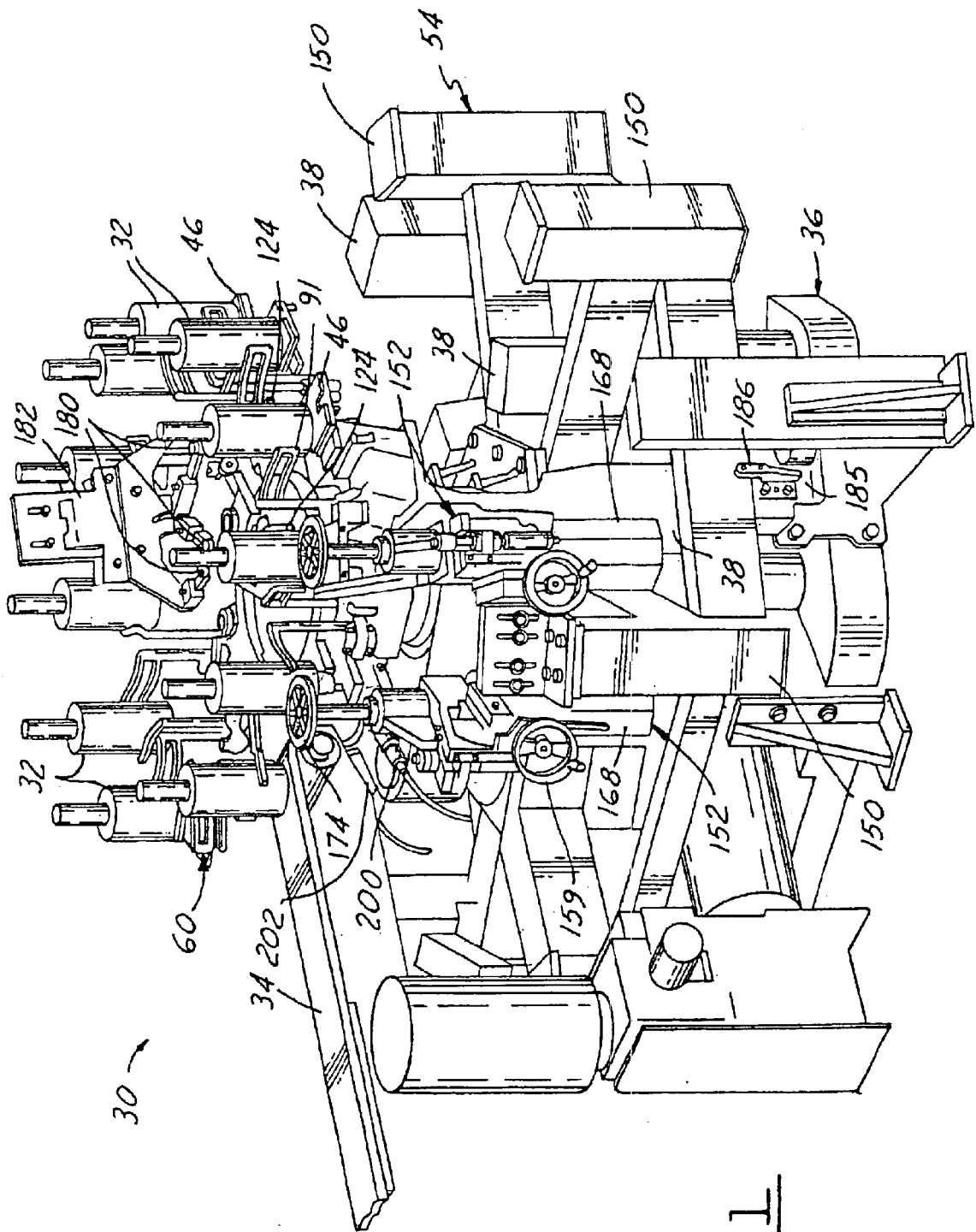
FIG. 1 is a fragmentary perspective view of an apparatus for indexing glassware through a series of stations in accordance with a presently preferred embodiment of the invention with portions removed to illustrate details.
Figure 2:
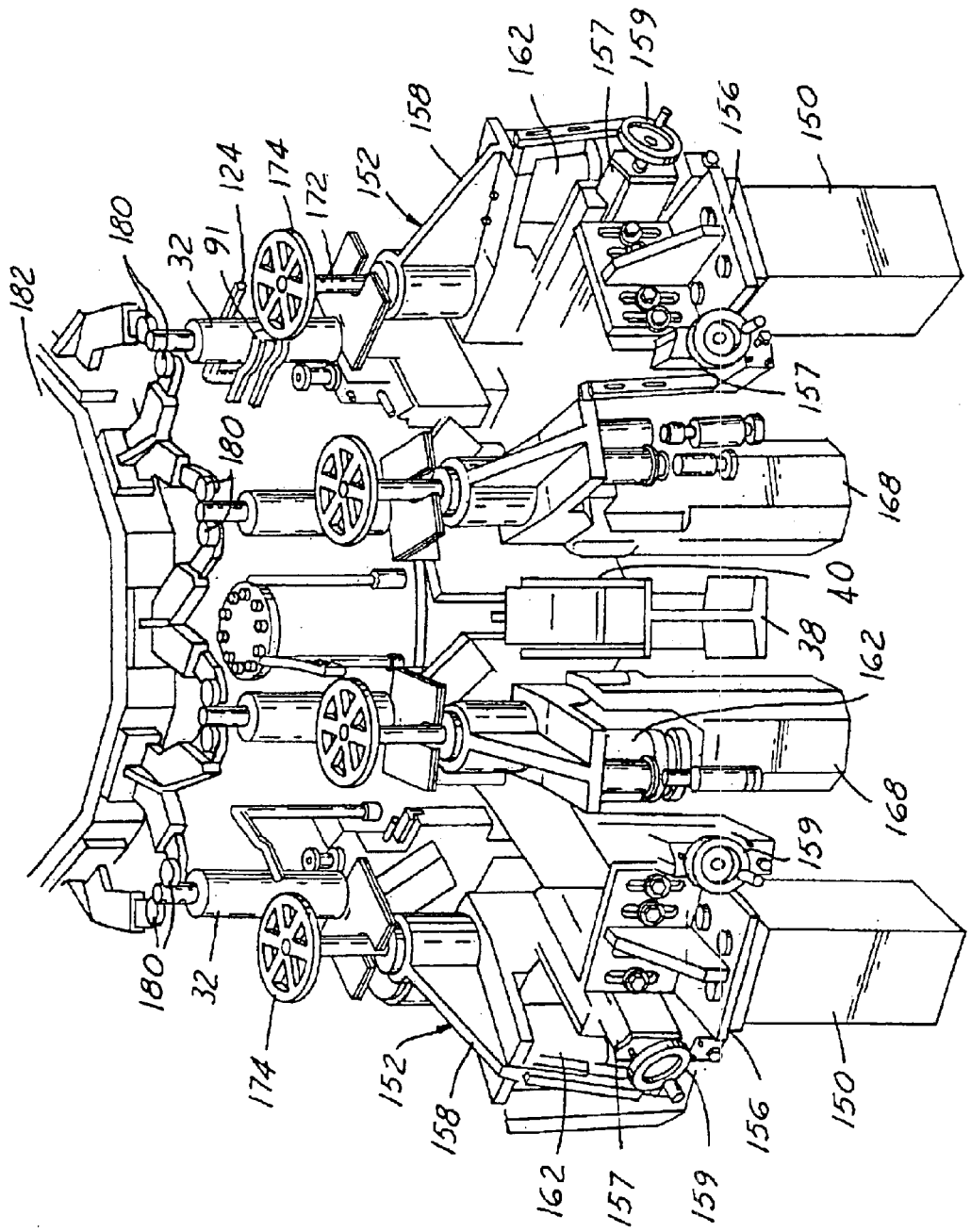
FIG. 2 is a fragmentary perspective view of the apparatus of FIG. 1 but with portions removed to illustrate details.
Figure 22:
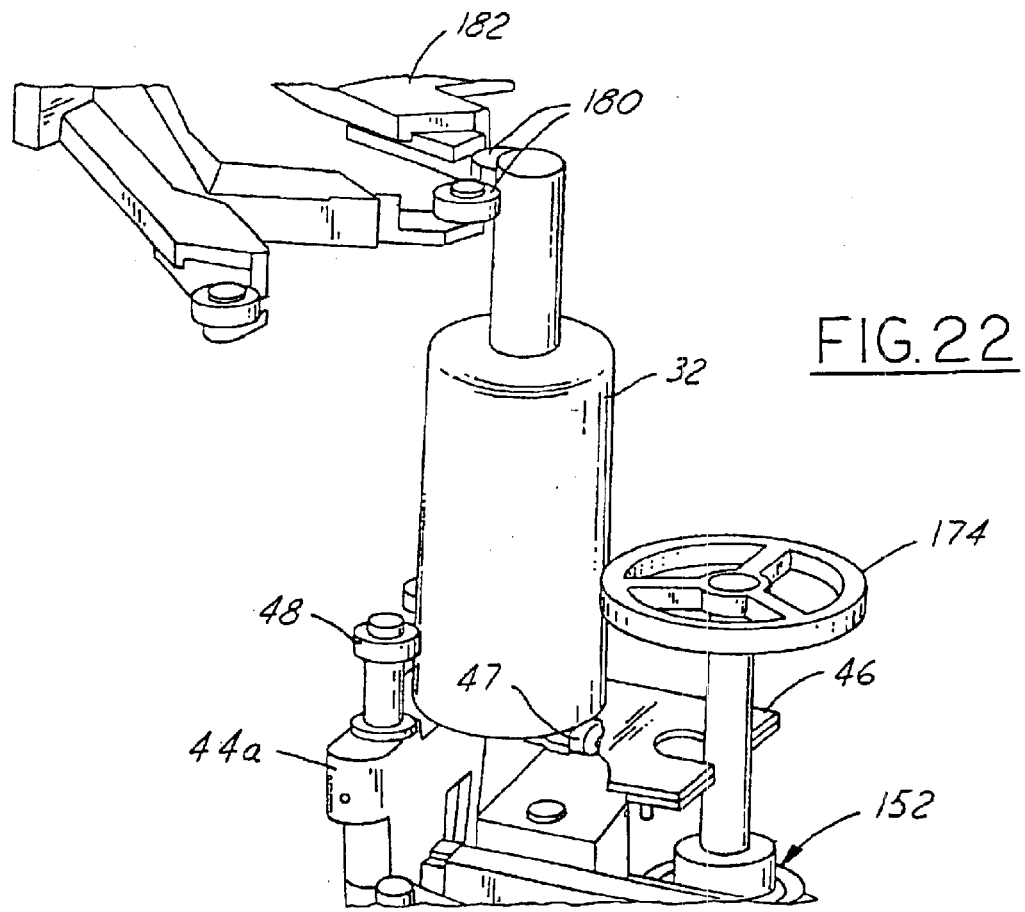
FIG. 22 is a fragmentary perspective view of a container engaged by drive and back-up rollers at one station of the apparatus of FIG. 1.
Figure 23:
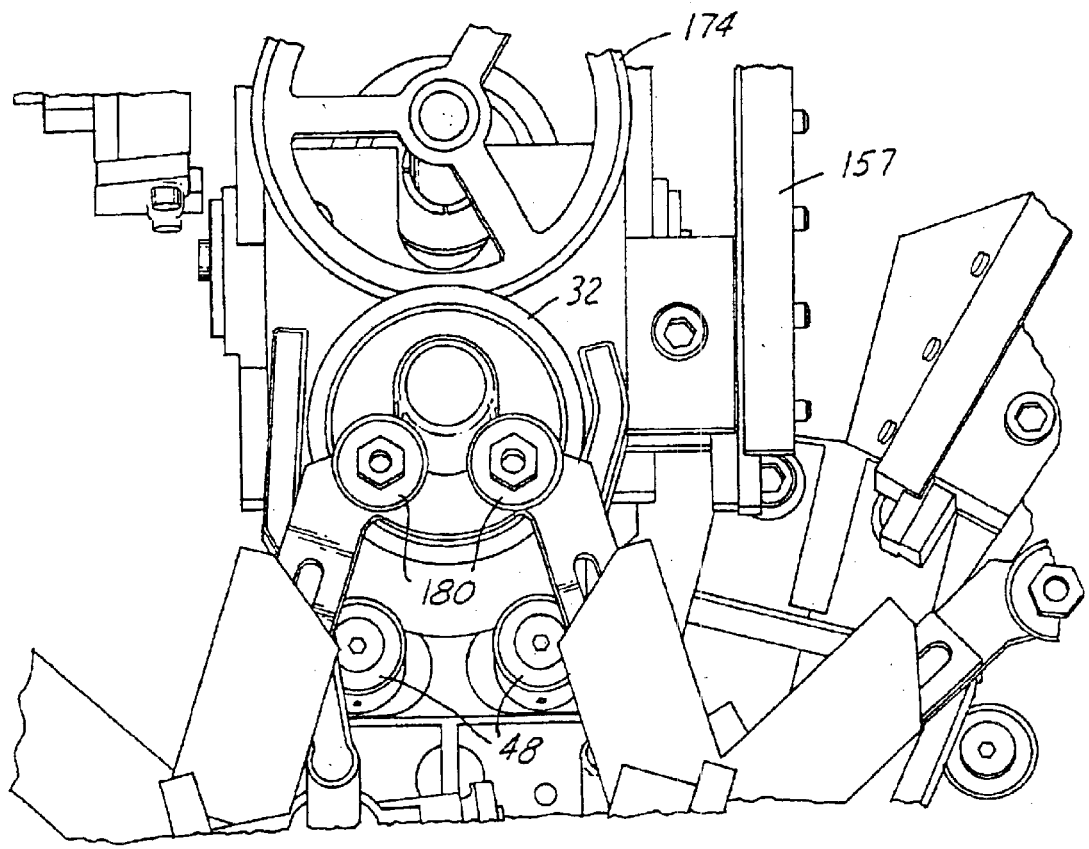
FIG. 23 is a fragmentary perspective view of a container at an inspection station engaged by drive and back-up rollers.

With the containers gripped between the fingers, carriers 70, 88 are simultaneously rotated clockwise by motors 66, 72 over an arc of 30° in the illustrated embodiment of the invention so as to increment the containers to the next stations. At least one of the carriers 70, 88 is then rotated away from the other (i.e., clockwise for carrier 70 and counterclockwise for carrier 88) under control of motors 66, 72 to deposit the containers at the next stations. The amount of rotation to release the containers is preset as a function of container diameter. At the inspection stations, the containers are released onto slide pads 46. Actuators 162 are then actuated by control electronics 184 to pivot container drive rollers 174 into radial engagement with the outside surfaces of the container sidewalls, and motors 168 are actuated to rotate rollers 174 and thereby rotate the containers about their central axes. Pivoting of the drive rollers into radial engagement with the containers pushes the containers into engagement with opposed lower back-up rollers 48 and upper back-up rollers 180 (FIGS. 22 and 23). At this point, the lower end of each container 32 is carried by support roller 47 at slide pad 46 (FIG. 22) to permit free rotation of the container about its axis. Actuators 162 at drive roller assemblies 152 push hard against the container upon initial engagement to rotate the container rapidly up to speed, and then reduce the force of engagement to reduce wear on the drive roller periphery. Actuators 162 then again push hard on containers 32 rapidly to decelerate rotation of the containers after inspection, so that the containers will be stationary when the drive roller assemblies are retracted and the containers are again engaged by the gripping fingers. Coils 162 are thus variably actuated by control electronics 184 during each inspection cycle. During such rotation, the containers are supported by back-up rollers 148 and finish back-up rollers 180 (FIG. 1). As each container is rotated, the inspection apparatus or system at the associated station is activated to inspect the container. At any station at which there is no inspection equipment or the inspection equipment is deactivated, drive roller actuator 162 and motor 168 are not energized. After an amount of time needed to complete the inspection process at each station, the process is repeated to grip the containers, increment the containers to the next stations, release the containers and activate the inspection equipment, etc.

There has thus been disclosed an apparatus and method for indexing glassware, such as containers, through a series of stations, such as container inspection stations, that fully satisfy all of the objects and aims previously set forth, both individually and collectively. A number of modifications and variations have been disclosed. Other modifications and variations will readily suggest themselves to persons of ordinary skill in the art. For example, servo ring motors can be used in place of the servo motor/gearbox coupling arrangements illustrated in FIGS. 11 and 12. The invention is intended to encompass all such modifications and variations as fall within the spirit and broad scope of the appended claims.

What is claimed is:

1. Apparatus for indexing glassware through a series of stations for inspection of the glassware, which includes:
    first and second circumferential arrays of alternately opposed glassware gripping fingers,
    first and second carriers respectively mounting said first and second finger arrays for rotation about a common axis,
    a first rotary electric servo motor coupled to said first carrier for rotating said first carrier about said common axis,
    a second rotary electric servo motor coupled to said second carrier for rotating said second carrier about said common axis, and
    control electronics coupled to said first and second motors for timing operation of said first and second servo motors relative to each other.

2. The apparatus set forth in claim 1 wherein said first carrier overlies said second carrier, wherein first motor is coupled to said first carrier by a shaft that extends along said common axis, and wherein said second motor is coupled to said second carrier by a sleeve that surrounds said shaft.

3. The apparatus set forth in claim 1 further including a drive roller at at least one of the inspection stations for engaging an article of glassware at said at least one station and rotating the article about its axis, and a third rotary electric servo motor coupled to said at least one drive roller, said third rotary electric servo motor being coupled to said control electronics for timing operation of said third motor relative to operation of said first and second motors.

4. The apparatus of claim 3 wherein said timing operation of said third motor permits said control electronics to determine the rotational position of an article of glassware as it is rotated and after it is rotated by said drive roller.

5. The apparatus set forth in claim 3 further including a pair of backup rollers disposed at said at least one station in stationary position relative to said carriers, said backup rollers engaging said article of glassware during rotation by said drive roller.

6. The apparatus set forth in claim 5 further including means for adjusting location of said pair of back-up rollers with respect to said carriers.

7. The apparatus set forth in claim 5 further including an actuator coupled to said at least one drive roller for selectively urging said drive roller against an article of glassware at the station, and a sensor coupled to said actuator for indicating absence of an article of glassware at the station as a function of overtravel of said drive roller toward said backup rollers.

8. The apparatus of claim 1 which also includes a lift frame that carries said first and second carriers, said lift frame being adjustable to vary the position of the first and second carriers.

9. The apparatus of claim 8 wherein the lift frame is adjustable to move the first and second carriers relative to an axis of articles of glassware engaged by said gripping fingers as said glassware is indexed through said series of inspection stations.

10. The apparatus of claim 9 wherein said lift frame includes a linear actuator that permits adjustment of the lift frame.

11. The apparatus of claim 9 wherein said linear actuator is driven by a servo controlled motor.

12. The apparatus of claim 8 wherein said first and second rotary electric servo motors are carried by the lift frame.

13. The apparatus of claim 3 which also includes a lift frame that carries said drive roller, said lift frame being adjustable to vary the position of the drive roller relative to said article of glassware.

14. The apparatus of claim 12 wherein the first and second carriers are carried by the lift frame to adjust the position of the first and second carriers relative to and along an axis of an article of glassware to be moved by the carriers.

15. The apparatus of claim 1 which also includes a support to position an article of glassware for inspection and wherein said first and second carriers are rotatable in opposed directions to alternately engage and disengage said fingers from an article of glassware, and said fingers are disengaged from said article of glassware when said article of glassware is positioned by said support.

16. The apparatus of claim 15 wherein said support includes a drive roller capable of engaging an article of glassware and rotating the article of glassware.

17. The apparatus of claim 15 wherein said support includes at least one back-up roller for supporting the article of glassware against said drive roller.

18. The apparatus of claim 1 which also includes a first set of support posts, a plurality of pads carried by the first set of support posts to receive articles of glassware on the pads for inspection of the articles, and a second set of support posts on which said first and second carriers are received.

19. The apparatus of claim 18 wherein said first set of support posts is substantially independent of said second set of support posts so that movement of said first and second carriages is isolated from said pads.

20. The apparatus of claim 18 which also includes a lift frame that includes said second set of support posts and is adjustable to vary the position of the first and second carriers relative to the pads.

21. The apparatus of claim 1 which also includes at least one sensor responsive to the position of at least one of the first and second carriers and in communication with the control electronics to permit said control electronics to determine the position of said at least one of the first and second carriers.

* * * * *